(12) United States Patent
Depa et al.

(10) Patent No.: US 11,231,411 B2
(45) Date of Patent: Jan. 25, 2022

(54) MOBILE DEVICE MULTI-ANALYTE TESTING ANALYZER FOR USE IN MEDICAL DIAGNOSTIC MONITORING AND SCREENING

(71) Applicant: Jana Care, Inc., Boston, MA (US)

(72) Inventors: Michal Depa, Beaconsfield (CA); Sidhant Jena, Boston, MA (US); Gaurav Rohatgi, Waltham, MA (US); Aron O. Zingman, Cambridge, MA (US)

(73) Assignee: Jana Care, Inc., Boston, MA (US)

( * ) Notice: Subject to any disclaimer, the term of this patent is extended or adjusted under 35 U.S.C. 154(b) by 0 days.

(21) Appl. No.: 16/593,099

(22) Filed: Oct. 4, 2019

(65) Prior Publication Data

US 2020/0096501 A1 Mar. 26, 2020

Related U.S. Application Data

(62) Division of application No. 14/997,749, filed on Jan. 18, 2016, now Pat. No. 10,436,773.

(51) Int. Cl.
*G01N 33/00* (2006.01)
*G01N 33/52* (2006.01)
(Continued)

(52) U.S. Cl.
CPC ............. *G01N 33/521* (2013.01); *A61B 5/00* (2013.01); *A61B 5/14532* (2013.01);
(Continued)

(58) Field of Classification Search
CPC .................................................. G01N 33/521
(Continued)

(56) References Cited

U.S. PATENT DOCUMENTS 4,772,561 A 9/1988 Genshaw
4,816,224 A 3/1989 Vogel et al.
(Continued)

FOREIGN PATENT DOCUMENTS

BR 112018014560 A2 12/2018
CN 1672631 A 9/2005
(Continued)

OTHER PUBLICATIONS

Millipore, "Rapid Lateral Flow Test Strips," 2002, 42 pages.
(Continued)

*Primary Examiner* — Christine T Mui
*Assistant Examiner* — Emily R. Berkeley
(74) *Attorney, Agent, or Firm* — Patterson Thuente Pedersen, P.A.

(57) ABSTRACT

A mobile device based multi-analyte testing analyzer for use in medical diagnostic monitoring and screening, and a method of manufacturing the same are disclosed. A reflectance based, colorimetric test strip reader for use with a mobile device having a jack plug receiving socket, said test strip reader adapted for removably receiving a test strip having a test strip longitudinal axis, comprising a housing; a jack plug operably coupled to and extending from said housing and adapted for operable coupling with said jack plug receiving socket; a test strip adapter including structure defining a test strip receiving channel; a light source oriented within said housing for directing light toward said test strip receiving channel to illuminate a test strip arranged within said test strip adapter; and a light sensor oriented within said housing to sense light reflected from a test strip carried by said test strip receiving channel.

13 Claims, 11 Drawing Sheets

(51) Int. Cl.

| | | |
|---|---|---|
| *A61B 5/00* | (2006.01) | |
| *A61B 5/145* | (2006.01) | |
| *A61B 10/00* | (2006.01) | |
| *G01N 21/84* | (2006.01) | |
| *A61B 5/157* | (2006.01) | |
| *G01N 33/50* | (2006.01) | |
| *A61B 5/15* | (2006.01) | |
| *B01L 3/00* | (2006.01) | |
| *G01N 21/78* | (2006.01) | |
| *H04M 1/21* | (2006.01) | |
| *A61B 5/1455* | (2006.01) | |
| *A61B 5/1477* | (2006.01) | |
| *H04M 1/72409* | (2021.01) | |
| *G01N 21/77* | (2006.01) | |

(52) U.S. Cl.
CPC ........ *A61B 5/157* (2013.01); *A61B 5/150022* (2013.01); *A61B 5/150358* (2013.01); *A61B 5/6898* (2013.01); *A61B 10/0045* (2013.01); *B01L 3/52* (2013.01); *G01N 21/78* (2013.01); *G01N 21/8483* (2013.01); *G01N 33/50* (2013.01); *G01N 33/52* (2013.01); *A61B 5/1455* (2013.01); *A61B 5/1477* (2013.01); *A61B 5/14507* (2013.01); *A61B 5/14546* (2013.01); *A61B 2010/0006* (2013.01); *A61B 2560/045* (2013.01); *A61B 2562/0295* (2013.01); *B01L 2300/023* (2013.01); *B01L 2300/0645* (2013.01); *B01L 2300/0654* (2013.01); *B01L 2300/0825* (2013.01); *B01L 2300/168* (2013.01); *G01N 2021/7759* (2013.01); *G01N 2021/7773* (2013.01); *G01N 2201/0627* (2013.01); *H04M 1/21* (2013.01); *H04M 1/72409* (2021.01); *H04M 2250/12* (2013.01)

(58) Field of Classification Search
USPC ......................................................... 436/165
See application file for complete search history.

(56) References Cited

U.S. PATENT DOCUMENTS

| | | | |
|---|---|---|---|
| 5,112,124 | A | 5/1992 | Harjunmaa et al. |
| 5,186,843 | A | 2/1993 | Baumgardner et al. |
| 5,304,468 | A | 4/1994 | Phillips et al. |
| 5,372,135 | A | 12/1994 | Mendelson et al. |
| 5,379,214 | A | 1/1995 | Arbuckle |
| 5,506,144 | A | 4/1996 | Sundrehagen |
| 5,597,532 | A | 1/1997 | Connolly |
| 5,622,868 | A | 4/1997 | Clarke et al. |
| 5,631,364 | A | 5/1997 | Sundrehagen et al. |
| 5,702,952 | A | 12/1997 | Sundrehagen et al. |
| 5,919,708 | A | 7/1999 | Sundrehagen |
| 6,024,919 | A | 2/2000 | Nelson et al. |
| 6,106,732 | A | 8/2000 | Johnston et al. |
| 6,295,506 | B1 | 9/2001 | Heinonen et al. |
| 6,491,870 | B2 | 12/2002 | Patel et al. |
| 6,574,425 | B1 | 6/2003 | Weiss et al. |
| 6,628,829 | B1 | 9/2003 | Chasen |
| 7,041,468 | B2 | 5/2006 | Drucker et al. |
| 7,045,361 | B2 | 5/2006 | Heiss et al. |
| 7,414,758 | B2 | 8/2008 | Vaughn |
| 7,507,550 | B2 | 3/2009 | Spinke et al. |
| 7,514,039 | B2 | 4/2009 | Loomis et al. |
| 7,809,418 | B2 | 10/2010 | Xu |
| 7,830,519 | B2 | 11/2010 | Mah et al. |
| 7,935,307 | B2 | 5/2011 | Angelides |
| 8,009,884 | B2 | 8/2011 | Chio |
| 8,145,431 | B2 | 3/2012 | Kloepfer et al. |
| 8,158,080 | B2 | 4/2012 | Bae et al. |
| 8,172,994 | B2 | 5/2012 | Lee |
| 8,204,566 | B2 | 6/2012 | Schurman et al. |
| 8,372,630 | B2 | 2/2013 | Uematsu et al. |
| 8,391,945 | B2 | 3/2013 | Say et al. |
| 8,394,328 | B2 | 3/2013 | Neel et al. |
| 8,467,843 | B2 | 6/2013 | Markle et al. |
| 8,597,188 | B2 | 12/2013 | Bernstein et al. |
| 8,700,115 | B2 | 4/2014 | Markle et al. |
| 8,935,007 | B2 | 1/2015 | Kloepfer et al. |
| 9,241,663 | B2 | 1/2016 | Jena et al. |
| 9,383,352 | B2 | 7/2016 | Nagalla et al. |
| 10,436,773 | B2 | 10/2019 | Depa et al. |
| 2002/0146345 | A1 | 10/2002 | Neilson et al. |
| 2003/0009088 | A1 | 1/2003 | Korth et al. |
| 2003/0050537 | A1 | 3/2003 | Wessel |
| 2003/0073243 | A1 | 4/2003 | Law et al. |
| 2003/0113227 | A1 | 6/2003 | Eyster et al. |
| 2003/0175806 | A1 | 9/2003 | Rule et al. |
| 2005/0095697 | A1 | 5/2005 | Bachur, Jr. et al. |
| 2005/0227370 | A1 | 10/2005 | Ramel et al. |
| 2006/0222567 | A1 | 10/2006 | Kloepfer et al. |
| 2006/0240541 | A1 | 10/2006 | Petruno et al. |
| 2006/0292039 | A1 | 12/2006 | Iida |
| 2007/0081920 | A1 | 4/2007 | Murphy et al. |
| 2007/0177032 | A1 | 8/2007 | Wong |
| 2008/0008370 | A1 | 1/2008 | Chio |
| 2008/0025599 | A1 | 1/2008 | Cho et al. |
| 2008/0166791 | A1 | 7/2008 | Kim et al. |
| 2009/0093012 | A1 | 4/2009 | Bae et al. |
| 2009/0163415 | A1 | 6/2009 | Katrukha et al. |
| 2009/0227855 | A1 | 9/2009 | Hill et al. |
| 2010/0044441 | A1 | 2/2010 | Cohen et al. |
| 2010/0110439 | A1* | 5/2010 | Gruler .................. G01N 21/645 356/440 |
| 2010/0145733 | A1 | 6/2010 | Drucker et al. |
| 2010/0222648 | A1 | 9/2010 | Siekmann |
| 2010/0254581 | A1 | 10/2010 | Nesser et al. |
| 2010/0312483 | A1 | 12/2010 | Peyser et al. |
| 2010/0317951 | A1 | 12/2010 | Rutkowski et al. |
| 2011/0019883 | A1 | 1/2011 | Bremnes et al. |
| 2011/0038765 | A1 | 2/2011 | Drucker et al. |
| 2011/0002613 | A1 | 10/2011 | Hannel et al. |
| 2011/0275162 | A1 | 11/2011 | Tong et al. |
| 2011/0308313 | A1 | 12/2011 | Azimi et al. |
| 2012/0082374 | A1 | 4/2012 | Agarwal et al. |
| 2012/0142084 | A1 | 6/2012 | Dunne et al. |
| 2012/0189509 | A1 | 7/2012 | Hsiao |
| 2012/0302456 | A1 | 11/2012 | Whitesides et al. |
| 2013/0083820 | A1 | 4/2013 | Barwell et al. |
| 2013/0276521 | A1 | 10/2013 | Fuerst et al. |
| 2014/0072189 | A1* | 3/2014 | Jena ..................... A61B 5/1455 382/128 |
| 2014/0009923 | A1 | 4/2014 | Tung et al. |
| 2014/0170757 | A1 | 6/2014 | Tsai et al. |
| 2014/0236489 | A1 | 8/2014 | Chen |
| 2014/0002713 | A1 | 9/2014 | Markovsky et al. |
| 2015/0160203 | A1 | 6/2015 | Choi et al. |
| 2015/0335272 | A1 | 11/2015 | Natale et al. |
| 2015/0359458 | A1 | 12/2015 | Erickson et al. |
| 2017/0234858 | A1 | 8/2017 | Depa et al. |
| 2018/0011105 | A1 | 1/2018 | Nakamura et al. |
| 2019/0187154 | A1 | 6/2019 | Kumar et al. |
| 2019/0232287 | A1 | 8/2019 | Depa et al. |

FOREIGN PATENT DOCUMENTS

| | | |
|---|---|---|
| CN | 102509064 A | 1/2008 |
| CN | 101545864 A | 9/2009 |
| CN | 101999881 A | 4/2011 |
| CN | 104812292 A | 7/2015 |
| CN | 206920451 U | 1/2018 |
| CN | 108712877 A | 10/2018 |
| EP | 1710565 A1 | 10/2006 |
| EP | 2104847 A4 | 1/2013 |
| EP | 2893477 A2 | 7/2015 |
| EP | 3405100 A4 | 10/2019 |
| EP | 3724659 A1 | 10/2020 |
| JP | 2007-523335 A | 8/2007 |
| JP | 2007-538230 A | 12/2007 |
| JP | 2008-286522 A | 11/2008 |

(56) References Cited

FOREIGN PATENT DOCUMENTS

| | | |
|---|---|---|
| JP | 2010-190867 A | 9/2010 |
| JP | 2014-185958 A | 10/2014 |
| JP | 2015-533211 A | 11/2015 |
| JP | 2016-509206 A | 3/2016 |
| JP | 6326574 B2 | 5/2018 |
| JP | 2019-510203 A | 4/2019 |
| KR | 10-2013-0066841 A | 6/2013 |
| KR | 1011454215 B1 | 10/2014 |
| WO | WO 1990/002950 A1 | 3/1990 |
| WO | WO 1999/022236 A1 | 5/1999 |
| WO | WO 2002/090995 A2 | 11/2002 |
| WO | WO 2008/086246 A1 | 7/2008 |
| WO | WO 2010/142447 A1 | 12/2010 |
| WO | WO 2011/023760 A1 | 3/2011 |
| WO | WO 2012/060810 A1 | 5/2012 |
| WO | WO 2013/028784 A1 | 2/2013 |
| WO | WO 2013/117233 A1 | 8/2013 |
| WO | WO 2014/037820 A2 | 3/2014 |
| WO | WO 2017/127349 A1 | 7/2017 |
| WO | WO 2019/118971 A1 | 6/2019 |
| WO | WO 2019/152508 A1 | 8/2019 |

OTHER PUBLICATIONS

Molecular Probes, "FluoSpheres Europium Luminescent Microspheres," Invitrogan, 2009, 3 pages.

Aviad, "Dario—Turning Your Smartphone into a Glucose Meter," Dec. 5, 2012, 4 pages.

Ballard, "Generalizing the Hough Transform to Detect Arbitrary Shapes," vol. 13, No. 2, p. 111-122, Oct. 10, 1979, 12 pages.

Canny, "A Computational Approach to Edge Detection," IEEE Trans. Pattern Analysis and Machine Intelligence, 8(6), pp. 679-698, 1986.

Cass, "Modified iPhone Can Detect Blood Disorders," Technology Review, Oct. 5, 2011, 2 pages.

Darma, "iPhone Transformed into Microscope and Spectrometer," Medgadget, Oct. 4, 2011, 3 pages.

Dell, et al., "Towards a Point-of-Care Diagnostic System: Automated Analysis of Immunoassay Test Data on a Cell Phone," NSDR, Jun. 28, 2011, 6 pages.

Dolan, "Misfit Wearables launches Shine, an elegant but rugged activity tracker," mobihealthnews, Nov. 14, 2012, 5 pages.

Duda, et al., "Use of the Hough Transformation to Detect Lines and Curves in Pictures," Communications of the ACM, vol. 15, Jan. 1972, 5 pages.

Džimbeg-Malčić, V., Barbarić-mikočević, Ž. & Itrić, K. Kubelka-Munk Theory in Describing Optical Properties of Paper ( I ); 1, 117-124 (2011) (Kubelka Munk theory), 8 pages.

EIN Presswire, "Philosys, Inc. Receives FDA Approval for Gmate VOICE Blood Glucose Meter," Mar. 18, 2013, 2 pages.

Frantzen, F. et al. Glycohemoglobin filter assay for doctors' offices based on boronic acid affinity principle. Clin. Chem. 43, 23 90-23 96 (1997) (K/S computation for glycated hemoglobin), 7 pages.

Ignac et al., "Piddle Simple, personal, urine analysis," 2012, 5 pages.

Jung et al., "Rectangle Detection based on a Windowed Hough Transform," In Proceedings of the Computer Graphics and Image Processing, XVII Brazilian Symposium, IEEE Computer Society, 113-120, 2004.

Kerr, "Urine sample app lets users detect diseases with iPhones," Feb. 27, 2013, 2 pages.

Klein, "The Latest on Cellscope's Smartphone-Based Microscope and Otoscope," Jun. 21, 2012, 3 pages.

KurzweilAI—Accelerating Intelligence.News, "Students' cellphone screening device for anemia wins $250,000 prize," Jul. 26, 2012, 2 pages.

Lee, et al., "A Simple and Smart Telemedicine Device for Developing Regions: A Pocket-Sized Colorimetric Reader," Lab Chip. 2011, 11, 120, pp. 120-126, revised Jul. 19, 2010, 7 pages.

Medgadget, "Dario Smartphone Powered Glucose Monitor," Medicine, Net News, Pediatrics, Sep. 9, 2013, 3 pages.

Medgadget, "Medgadget Cell Phone-Based Imaging Technique to Read ELISA Results," Sep. 2011, 2 pages.

Microchip, Low-Power Linear Active Thermistor™, 2009, 24 pages.

Mudanyali et al., "Integrated Rapid-Diagnostic-Test Reader Platform on a Cellphone," LAB on a Chip, vol. 12, No. 15, Apr. 16, 2012, 17 pages.

National Semi Conductor, "LPV7215 580 nA Rail-to-Rail Input and Output, 1.8V, Push-Pull Output Comparator," Sep. 2005, 7 pages.

Ostrovsky, "iBGstar Glucometer for iPhone Now Available in U.S.," May 4, 2012, 5 pages.

Ostrovsky, "iExaminer iPhone Adapter for Welch Allyn's PanOptic Ophthalmoscope Cleared in U.S, (w/video)," Jan. 24, 2013, 3 pages.

Ostrovsky, "Presentations from Health Hack Day Now available for Online Viewing," May 22, 2012, 4 pages.

PR Newswire, "Philosys Awarded CE Mark for new Gmate® SMART meter and seeks global telecommunications partners," Aug. 13, 2012, 2 pages.

PR Newswire, "Philosys Awarded CE Mark for New Gmate® SMART Meter an Seeks Global Telecommunications Partners," Aug. 13, 2012, 1 page.

PR Newswire, "Philosys, Inc. anticipates FDA Approval for New Gmate Blood Glucose Monitoring System," Aug. 2, 2012, 2 pages.

PR Newswire, "The New iPhone 5 and Gmate SMART Create a Dynamic Duo in Medical Diagnostics," Sep. 25, 2012, 2 pages.

Science Daily, "Hold the Phone for Vital Signs: Researchers Turn a Smart Phone into a Medical Monitor," Oct. 6, 2011, 3 pages.

Shen, et al., "Point-of-care colorimetric detection with a smartphone," Jul. 1, 2012, 4 pages.

Szeliski, "Computer Vision: Algorithms and Applications," Sep. 3, 2010, pp. 80-84 (Section 2.3.2).

Taos, "TCS3472 Color Light-To-Digital Converter with IR Filter," Texas Advanced Optoelectronic Solutions, Inc., Aug. 2012, 26 pages.

Texas Instruments, "100ppm/°C, 50 µA in SOT23-3 CMOS Voltage Reference," Jun. 2002, 16 pages.

Wakefield; "TED 2013, Uchek app tests urine for medical issues," BBC News Technology, Feb. 27, 2013, 4 pages.

Wang, et al., "Integration of cell phone imaging with microchip ELISA to detect ovarian cancer HE4 biomarker in urine at the point-of-care," Lab Chip, 11(20), pp. 3411-3418, Oct. 21, 2011, 16 pages.

PCT/US2017/013736, Search Report and Written Opinion, dated Apr. 25, 2017, 13 pages.

European Application No. 17741806.8 Extended European Search Report dated Sep. 24, 2019, 10 pages.

Application and File History of U.S. Appl. No. 13/815,764, filed Mar. 15, 2013, now U.S. Patent No. 9,2241,663. Inventors Jena et al.

Application and File History of U.S. Appl. No. 14/997,749, filed Jan. 18, 2016, now U.S. Patent No. 10,436,773. Inventors Depa et al.

CN 201780012205.3, First Office Action dated Dec. 2, 2020, 7 pages.

\* cited by examiner

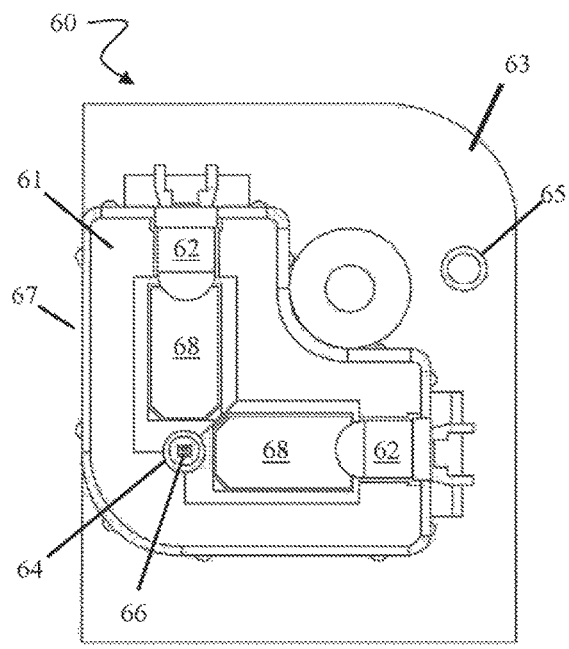
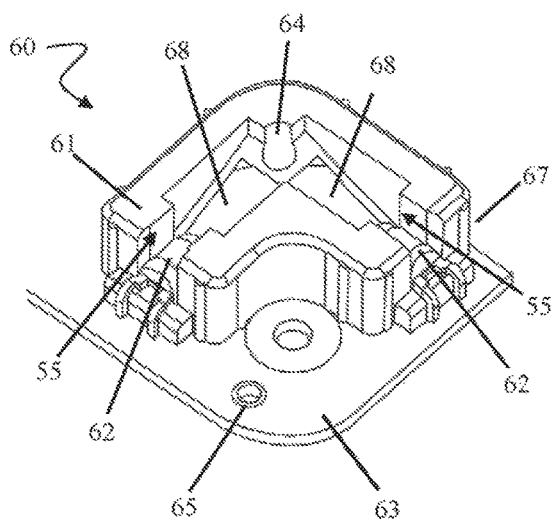
FIG. 4A
FIG. 4B
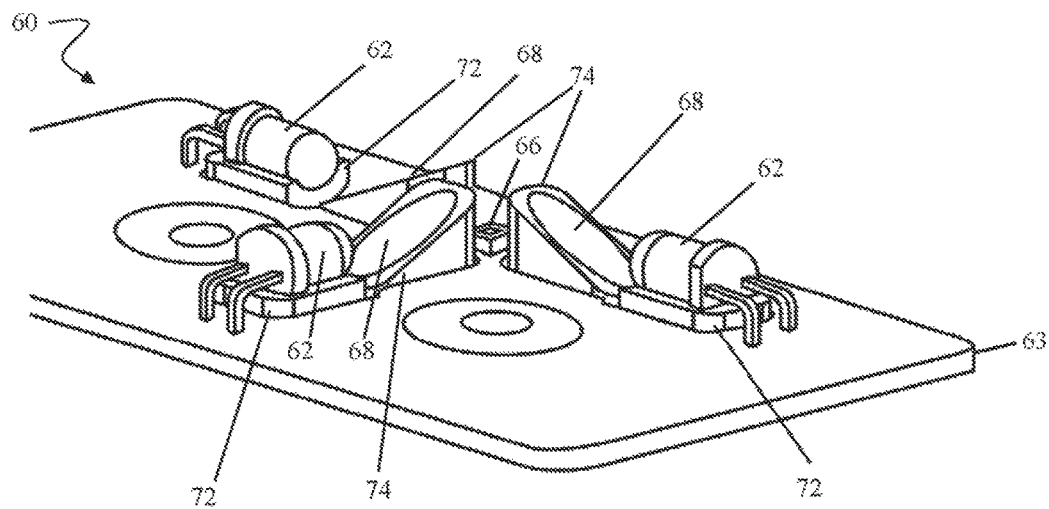
FIG. 4C

MOBILE DEVICE MULTI-ANALYTE TESTING ANALYZER FOR USE IN MEDICAL DIAGNOSTIC MONITORING AND SCREENING

RELATED APPLICATION

This application is a division of U.S. patent application Ser. No. 14/997,749 filed Jan. 18, 2016, now U.S. Pat. No. 10,436,773 issued Oct. 8, 2019, which is hereby fully incorporated herein by reference.

FIELD OF THE INVENTION

The invention relates generally to bodily fluid testing systems, and more particularly to a mobile device based multi-analyte testing analyzer for use in medical diagnostic monitoring and screening.

BACKGROUND OF THE INVENTION

Bodily fluid testing systems can be used to detect various analyte concentrations within a bodily fluid sample to provide accurate and detailed medical information. Such information can be used to aid in the diagnosis and/or treatment of certain medical conditions such as diabetes. For example, in diabetic monitoring applications, analyzers can be used by diabetic patients or physicians to detect high (i.e., hyperglycemia) or low (i.e., hypoglycemia) blood glucose levels. The monitored levels can aid in the treatment and management of diabetes by notifying a user of abnormal levels, which allows the user to make necessary adjustments such as increasing sugar or insulin intake to stabilize blood glucose levels. As another example, HbA1c, which is also referred to as glycated hemoglobin, is an analyte used for both monitoring and screening of diabetes, as it captures the average plasma glucose concentration over prolonged periods. Other examples are analytes that are more general to other chronic conditions. Such examples include lipids (total cholesterol, HDL cholesterol, LDL cholesterol, and triglycerides), serum creatinine, hemoglobin, and ketones, which can be measured in various bodily fluids, such as blood, urine, and saliva. Currently, there are several systems and methods used in medical diagnostic monitoring and screening.

One conventional approach includes the use of a stand-alone test system to process and analyze data related to analyte concentrations within a measured sample of a fluid based on a reflectance reading from a reagent test strip. For example, in U.S. Pat. No. 5,304,468 to Phillips et al., a method is disclosed for taking a reflectance reading from a reagent pad that consists of a porous matrix. The reflectance reading is based upon a reflectance change resulting from penetration of the porous matrix by an aqueous solution. Another method is disclosed in U.S. Pat. No. 6,574,425 to Weiss et al., which uses an "ultra-sensitive" meter (a "reflectometer") to accurately resolve the full range of developed subtle color shade changes produced by the transdermal extraction of analytes.

Some other conventional approaches include the use of integrated systems comprising a blood glucose monitor and an external processing device for data management and analysis such as those disclosed in U.S. 2013/0276521 to Fuerst et. al, U.S. Pat. No. 7,935,307 to Angelides, and U.S. Published Application No. 20120142084 to Dunne et. al. Additionally, other integrated systems use naked mobile device connections, where, e.g., a rapid diagnostics test (RDT) is performed by generating a digital image of an RDT strip using a camera unit and software application running on a mobile device.

Drawbacks to such conventional approaches include the inability to accurately quantitatively analyze chemistries that have different reaction color spectra, to accommodate various test strip dimensions or to dynamically update system parameters according to various testing requirements. Thus, there is a need for an affordable and cost effective system that can perform an array of color analyses while being universal in design to accommodate various testing requirements.

SUMMARY OF THE INVENTION

The invention is generally directed to a system and method of measuring analyte concentrations in bodily fluids using a mobile device application as a user interface to control and process data from a reflectance based, colorimetric test strip reader.

One aspect of the invention is directed to a reflectance based, colorimetric test strip reader for use with a mobile device having a jack plug receiving socket, said test strip reader adapted for removably receiving a test strip having a test strip longitudinal axis, comprising a housing; a jack plug operably coupled to and extending from said housing along a jack plug axis and adapted for operable coupling with said jack plug receiving socket; a test strip adapter operably, removably coupled to said housing, said test strip adapter including structure defining a test strip receiving channel presenting a test strip receiving channel axis; a light source oriented within said housing for directing light toward said test strip receiving channel when said test strip adapter is operably coupled to said housing such that a test strip, when carried by said test strip receiving channel, is illuminated; and a light sensor oriented within said housing to sense light reflected from a test strip carried by said test strip receiving channel.

A related aspect of the invention is directed to a method of measuring analyte concentrations utilizing a reflectance based colorimetric test strip reader operably coupled with a mobile device, the method comprising receiving a bodily fluid sample on said test strip; activating a light source to illuminate a reaction area of a test strip in response to insertion of a test strip into a test strip receiving channel; determining an analyte concentration of said bodily fluid sample based on a color profile change of said test strip; and transmitting a signal corresponding to said analyte concentration to said mobile device.

Another aspect of the invention is directed to a method of using a test strip reader communicably coupled with a mobile device, the test strip reading having a housing, a jack plug, a test strip adapter including a test strip receiving channel, and an optical sub-system, the method comprising activating a light to illuminate a reaction area of a test strip in response to insertion of a test strip into the test strip receiving channel; illuminating a reaction area of said test strip utilizing a light source of said optical sub-system; detecting a bodily fluid sample deposited on said test strip; determining an analyte concentration of said bodily fluid sample based on a color profile change of said test strip; and transmitting a signal corresponding to said analyte concentration to said mobile device.

A still further aspect of the invention is directed to a method comprising providing a test strip reader to a user, the test strip reader including a housing, a jack plug, a test strip adapter and an optical sub-system; and providing instructions to the user for performing an analyte analysis test with the test strip reader, the instructions comprising coupling the test strip reader to a mobile device; inserting a test strip into an adapter channel of said test strip adapter; receiving a bodily fluid sample on said test strip; causing said test strip reader to measure an analyte concentration of said bodily fluid sample; and causing said test strip reader to transmit data corresponding to an analyte concentration to said mobile device for display on a graphical user interface.

BRIEF DESCRIPTION OF THE DRAWINGS

Embodiments of the present invention may be more completely understood in consideration of the following detailed description of various embodiments of the invention in connection with the accompanying drawings, in which:

FIG. 4A depicts a top plan view of an optical sub-system according to an embodiment.

FIG. 4B depicts an isometric view of an optical sub-system according to an embodiment.

FIG. 4C depicts a perspective view of an optical sub-system according to another embodiment.

Figure 1:
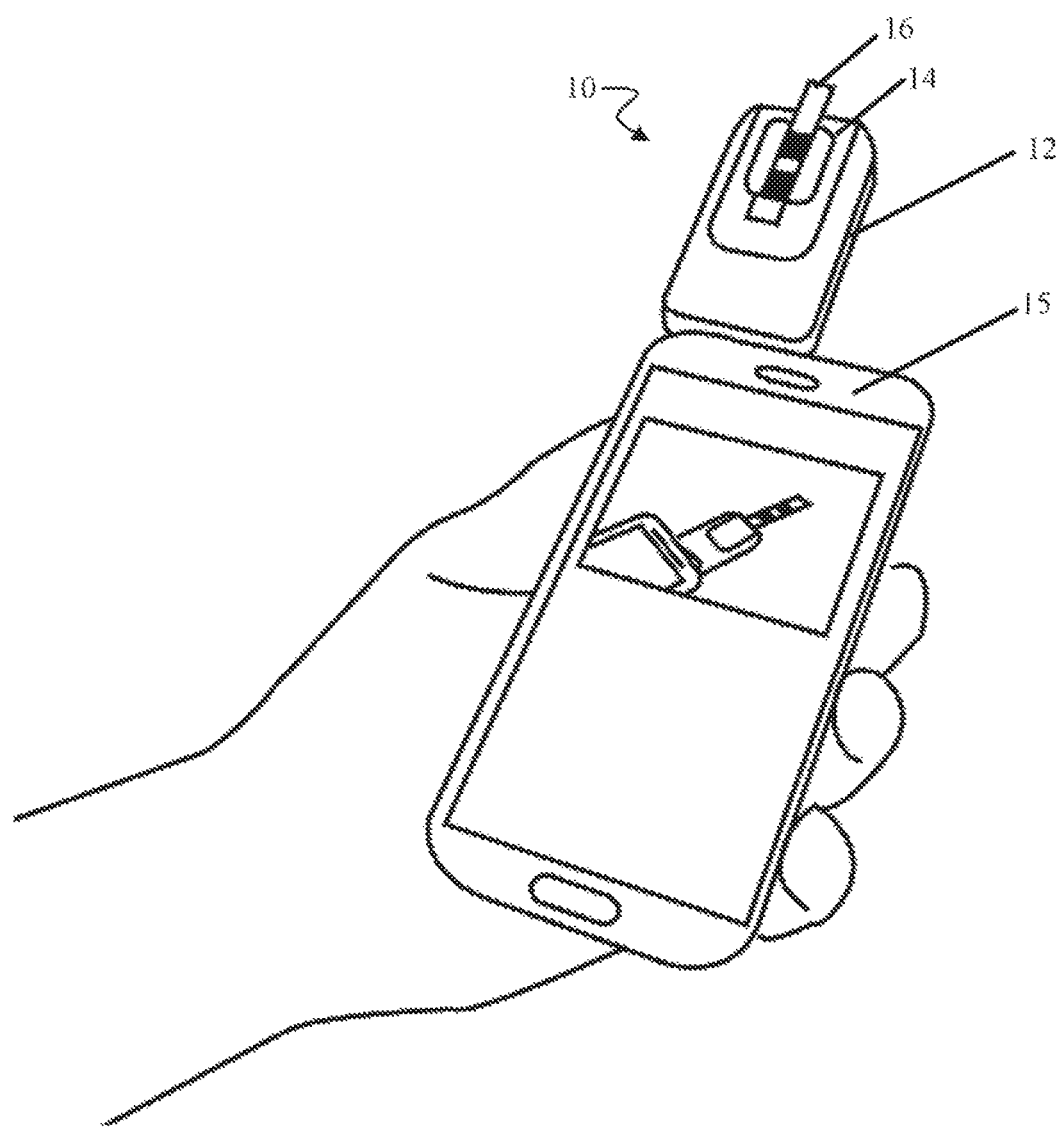
FIG. 1 depicts a test strip reader in use with a mobile device according to an embodiment.

While the various embodiments of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the inventions as may be claimed.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the inventions as claimed.

Embodiments herein relate to an analyte testing analyzer that interfaces with a mobile device for use in medical diagnostic monitoring and screening. In embodiments, the analyte testing analyzer comprises a reflectance-based colorimetric test strip reader comprising a modular test strip adapter. The modularity of the test strip adapter allows the reader to be quickly adapted to support a variety of colorimetric test strips used in different analyte concentration analysis tests. The reader further comprises a jack plug arranged at a lower end of the reader and which extends outwardly from the reader to communicatively couple the reader to the mobile device. Because the reader is simple and does not have any user interface such as a screen, an end user will interact with the reader through an application installed on the mobile device.

Moreover, a core function of the reader is to detect changes in the color profile of the colorimetric test strips in response to fluid samples deposited on the test strips utilizing an optical sub-system housed within the reader. In embodiments, the optical sub-system comprises at least two light emitting diodes (LEDs) and a light sensor arranged in between the diodes. The optical sub-system and test strip reaction pad is optically aligned so that incident light from the LEDs gets reflected from the reaction pad and is detected by the light sensor. During an analysis, the reader continuously sends raw data (that includes the detected color of the test strip's reaction pad as measured by the light sensor) to the mobile device through the jack plug. The change in color is then mapped to the concentrations of one of several analyte concentrations in the bodily fluid such as glucose, HbA1c, lipids (total cholesterol, HDL cholesterol, LDL cholesterol, and triglycerides), serum creatinine, hemoglobin, and ketones, which are pre-programmed in the software application of the mobile device.

Figure 2A:
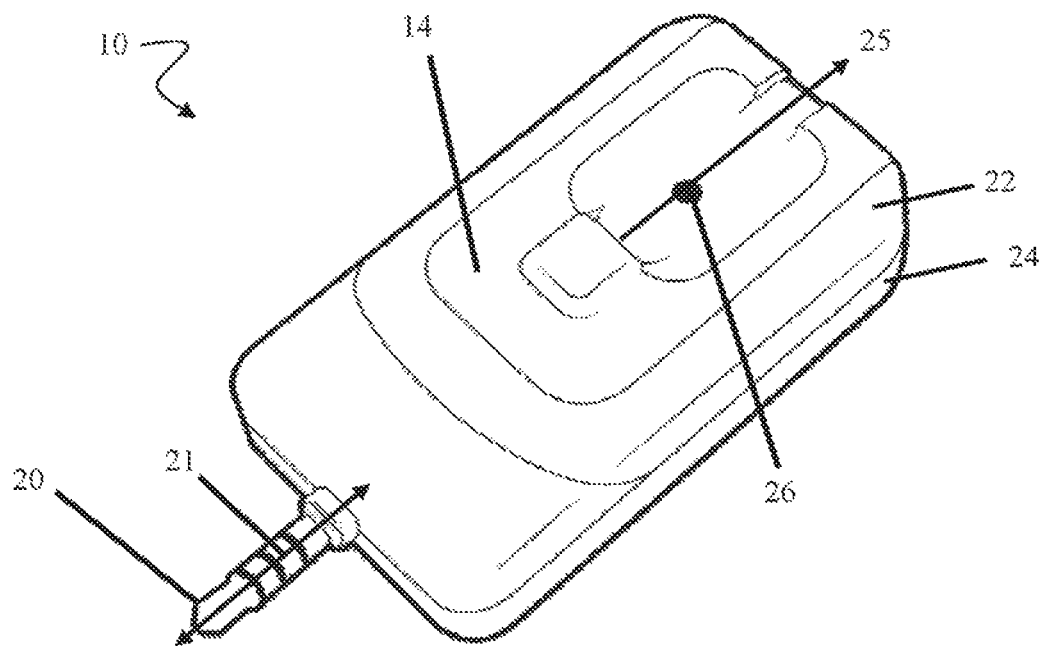
FIG. 2A depicts a perspective view of a test strip reader according to an embodiment.
Figure 2B:
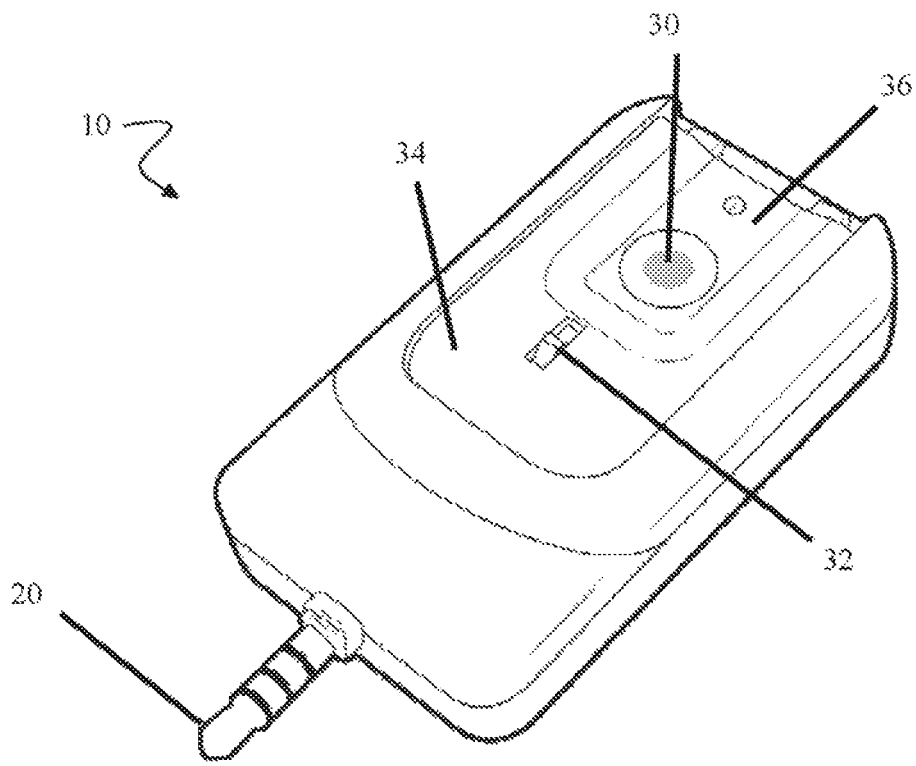
FIG. 2B depicts a perspective view of the test strip reader of FIG. 2A according to an embodiment.

Referring now to FIGS. 1, 2A and 2B, a colorimetric test strip reader 10 adapted for coupling with a mobile device 15 is depicted. Although depicted in FIG. 1 as being a mobile phone, mobile device 15 can be any mobile device with programming and computing capabilities such as smart phones, tablets, personal digital assistants (PDA), laptop computers, or other suitable computing devices in various embodiments.

In example embodiments, test strip reader 10 comprises a housing 12, a jack plug 20 that is used to couple test strip reader 10 to mobile device 15, and a test strip adapter 14 removably and operably coupled to housing 12 and configured to receive a test strip 16. Housing 12 can comprise a top portion 22 and a bottom portion 24 coupled together to form an enclosure for accommodating various components (e.g., optical sub-system 60, printed circuit boards, power supply, battery, etc.) encased within test strip reader 10. As a result of the portable design of test strip reader 10, housing 12 is sized relatively small (e.g., 63 mm (length) by 36 mm (width) by 16 mm (height)) and is preferably formed of a lightweight material such as plastic or other suitable materials.

Figure 2C:
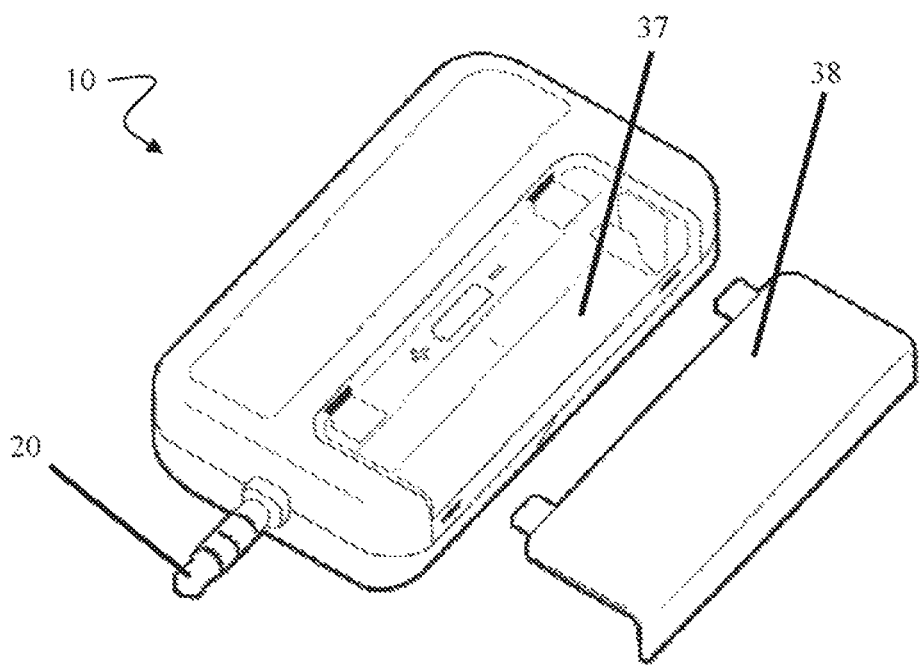
FIG. 2C depicts a perspective view of the test strip reader of FIG. 2A according to an embodiment.

To accommodate removable insertion of test strip adapter 14, top portion 22 of housing 12 can comprise an adapter channel 34 integrally formed in top portion 22 (see FIG. 2B). Adapter channel 34 can comprise a generally U-shaped structure comprising a plurality of grooves formed in or on an outer edge of channel 34 to receive a corresponding coupling feature of test strip adapter 14. As stated above, top portion 22 can be fixedly or removably coupled to bottom portion 24 utilizing various coupling mechanisms such as snap, sliding, or screw engagement. Additionally, because test strip reader 10 is preferably battery powered, bottom portion 24 can comprise a battery compartment 37 integrally formed in a side section of bottom portion 24 that can be sized to accommodate a single battery unit (see FIG. 2C). The battery compartment 37 can be closed with battery cover 38 that snaps into the housing 12 to stay in place.

As illustrated in FIG. 2B, removal of test strip adapter 14 from adapter channel 34 provides access to an optical window 30 that covers the optics of test strip reader 10 and a strip switch 32. In embodiments, optical window 30 can be formed in or on an optical cavity 36 arranged within adapter channel 34. Optical window 30 can comprise a generally circular, rectangular, or oval shape or some other suitable configuration in various embodiments. It should be noted, however, that the geometrical structure of optical window 30 is sized such that sufficient light is transmitted from light sources 62 to a reaction area of test strip 16 and back to the light sensor 66. Furthermore, insertion of test strip adapter 14 into adapter channel 34 aligns an optical aperture 26 above optical window 30 (refer, e.g., to FIG. 2A), such that a light path is defined which directs light from and back to an optical sub-system 60 (see FIGS. 4A, 4B and 4C).

In embodiments, strip switch 32 can be arranged proximate a base of optical cavity 36 and can comprise a roller lever arm toggle micro switch, an optical path detection switch, or other suitable switches. Strip switch 32 is arranged such that activation of strip switch 32 occurs upon insertion of test strip 16 into guiding rails 40 and 42. In other words, engagement of test strip 16 to strip switch 32 electrically couples the power supply of test strip reader 10 to light sources 62 and other electronic components of the test strip reader 10, thereby powering it on. In other embodiments, the test strip reader 10 can be powered on through a different mechanism and the status of strip switch 32 can be read by a microcontroller of test strip reader 10 and sent to mobile device 15 for interpretation by the mobile device application or display on a user interface.

Jack plug 20 can be arranged at a distal end of housing 12, such that a portion of jack plug 20 extends outwardly and away from housing 12 along a jack plug axis 21 to provide connectivity to mobile device 15. As illustrated in FIGS. 1 and 2A, jack plug axis 21 can be generally aligned with test strip receiving channel 25 such that insertion of a test strip 16 into channel 25 coaxially aligns a longitudinal axis of the test strip with jack plug axis 21, which minimizes the potential motion of test strip reader 10 as the test strip 16 is inserted. Although generally referred to herein as "jack plug," jack plug 20 can include any wired or wireless communication element including, but not limited to, universal serial bus (USB), including micro USB and mini USB, BLUETOOTH®, near field communication (NFC), or WLAN (any IEEE 802.11 variant).

In embodiments, test strip adapter 14 can be arranged at a proximal end of housing 12 opposite that of jack plug 20 and can be removably coupled to housing 12. Test strip adapter 14 is configured with a modular design that allows the unit to accommodate a variety of test strip dimensions and sizes. The modularity of test strip adapter 14 is a unique feature in comparison to other standard devices, and allows for test strip reader 10 to be easily adapted to support a multitude of colorimetric test strips by simply reconfiguring test strip adapter 14 to accommodate new strip dimensions. In addition, test strip adapter 14 can comprise a test strip receiving channel 25 and at least one optical aperture 26 arranged within test strip receiving channel 25 which will be discussed in greater detail with reference to FIGS. 3A and 3B.

While particular exemplary embodiments of test strip reader 10 are shown and described herein, it should be understood that the size, shape, and/or particular arrangement or number of components of test strip reader 10 may vary according to various embodiments. For example, in other embodiments, test strip reader 10 can further comprise a temperature sensor arranged within housing 10 to sense and monitor the ambient air conditions of test strip reader 10. This ambient temperature data can also be sent to mobile device 15 for monitoring, and appropriate information can be displayed on the user interface of mobile device 15, for instance, if the ambient temperature is outside of a certain allowable range.

Figure 3A:
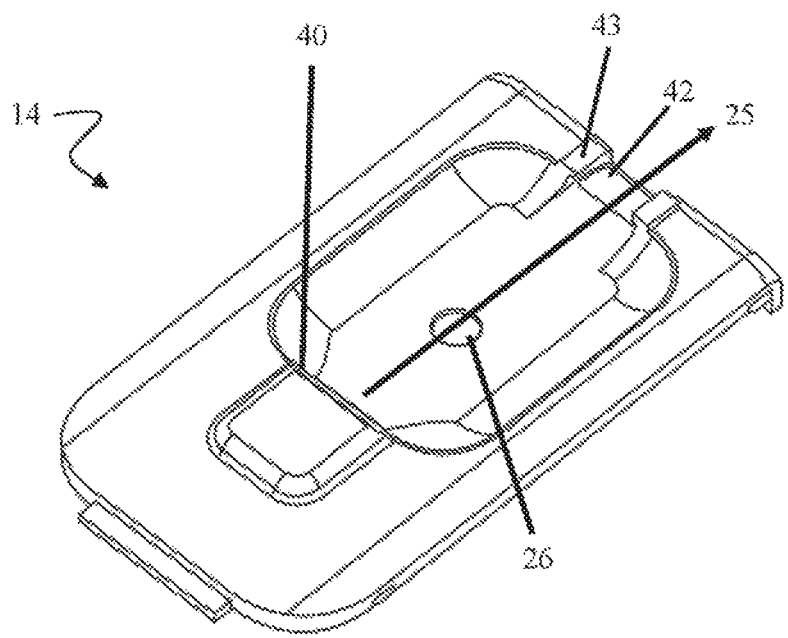
FIG. 3A depicts an isometric view of a test strip adapter according to an embodiment.
Figure 3B:
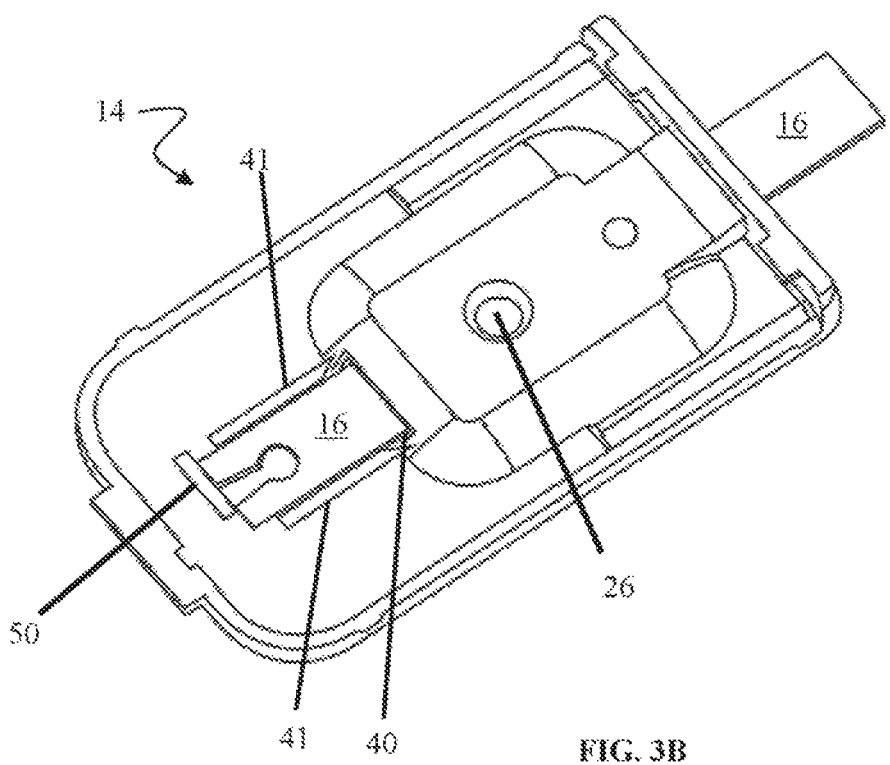
FIG. 3B depicts a underside view of a test strip adapter according to an embodiment.

Referring to FIGS. 3A and 3B, a front and rear view of test strip adapter 14 is shown according to an embodiment. As depicted, test strip adapter 14 can comprise a first test strip guiding rail 40 coaxially aligned with a second test strip guiding rail 42 to define a test strip receiving channel 25 for accommodating test strip 16. As depicted in FIG. 3A, embodiments, the strip guiding rail 42 may further include a small notch 43 (e.g., a bridge feature) to help secure placement of test strip 16 in the z-axis direction, but may vary in other embodiments. In other embodiments, for example, the strip guiding rail 42 can be configured without notch 43 or may be integrally formed with guiding rail 40 to include two or more notches 43 to accommodate various adapter configurations. In addition, as discussed with reference to FIG. 2A, test strip adapter 14 can comprise at least one optical aperture 26, formed in or on test strip receiving channel 34. FIG. 3B illustrates the underside view of test strip adapter 14 comprising optical aperture 26, first test strip guiding rail 40, secondary underside test strip guiding rails 41, a test strip stopping block 50 and test strip 16. Guiding rails 40, 41, 42 and test strip stopping block 50 in conjunction allow test strip 16 to be inserted in a repeatable manner into test strip reader 10. In various embodiments, the positioning and dimensions of test strip adapter 14 and its corresponding components (e.g., guiding rails 40, 41, 42 and stopping block 50) can be modified to allow for the use of strips 16 of different dimensions. Specifically, a change in the width or thickness of test strip 16 would induce changes in guiding rails 40, 41, 42, while a change in the distance from the front of test strip 16 to its reactive area would induce a change in the position of stopping block 50. For example, in the embodiment of FIG. 3B, stopping block 50 can accommodate strips of various lengths without modifications to its position, as long as the length of test strip 16 is larger than a certain minimum.

Referring to FIGS. 4A, 4B, and 4C, an optical sub-system 60 of test strip reader 10 is depicted according to an embodiment. In embodiments, optical sub-system 60 can comprise an optical block 67 arranged on a support structure 63. In embodiments, support structure 63 can comprise a circuit board, such as a printed circuit board (PCB), or any other suitable base structure. Additionally, it can be advantageous to size the geometrical dimensions of support structure 63 such that support structure 63 is configured for fitted insertion into housing 12. Various coupling mechanisms can be used for attaching support structure 63 to housing 12. For example, in one embodiment, support structure 63 can comprise at least one mounting hole 65 (see FIGS. 4A and 4B) for accommodating screw or other fasteners to secure support structure 63 to housing 12. In other embodiments, such as that of FIG. 4C, other coupling mechanisms can be used including, but not limited to adhesive bonding, snap connects, clamps, or brackets. The depictions of optical sub-system 60 in FIGS. 4A, 4B, and 4C are not to scale and are simply used to illustrate basic components and features of embodiments of optical sub-system 60. For example, the depiction of optical sub-system 60 in FIG. 4C is shown without body member 61 to better illustrate components such as reflective surfaces 68, light sources 62 and light sensor 66, which are discussed in further detail below.

In embodiments, optical block 67 can comprise a body member 61 comprising a generally L-shaped that defines a mounting channel 55 within a cross-sectional area of body member 61 to accommodate placement and/or mounting of components such as light source 62, light sensor 66, and reflective surfaces 68. For example, as depicted, optical sub-system 60 can include at least one reflective surface 68, at least one illuminating light source 62 arranged proximate reflective surfaces 68, and at least one light sensor 66.

As illustrated in FIGS. 4A and 4B, in embodiments, optical block 67 can further comprise a sensor well 64 arranged intermediately between reflective surfaces 68 at an end opposite the placement of light sources 62. This particular arrangement of sensor well 64 can be advantageous in selectively controlling the amount of light received within sensor well 64. In embodiments, light source 62 can comprise a light-emitting diode coupled to a bracket 72 to ensure proper alignment of light source 62 with reflective surfaces 68. Bracket 72 can be coupled to or arranged in apposition to each frame 74 of reflective surfaces 68 (see FIGS. 4A, 4B, and 4C). While depicted in this embodiment as an LED, it should be noted that light source 62 can include any device capable of illuminating light onto a surface of an object.

To detect light illuminated from light source 62, light sensor 66 can be arranged within optical sub-system 60, such that light reflected from test strip 16 is directed to sensor 66. In embodiments, light sensor 66 can be coupled to or arranged on support structure 63 and can be sized to fit within sensor well 64 as illustrated in FIG. 4A. Sensor 66 can comprise a photodiode, optical detector, phototransitors, photoresistors, or other suitable sensing elements in various embodiments. As discussed previously, the structural layout of optical sub-system 60 serves to illuminate the test strip 16 being imaged by using light sources 62 in conjunction with the inclined reflective surfaces 68 that direct the light at the reactive area of test strip 16. Some of the light reflected off test strip 16 can travel inside of light sensor well 64 where it eventually can get detected by the light sensor 66. This design minimizes the effect of specular reflection because of the mismatch between the incident angle of illumination onto the reactive area of test strip 16 and the angle between that reactive area and light sensor 66. This allows mostly diffuse reflected light to reach light sensor 66, which is known to be the type of light that carries the information about the surface color of the reactive area of test strip 16.

In embodiments, reflective surfaces 68 can comprise a reflective element, such as a mirror affixed to body member 61 or an angled frame 74. Although the depicted embodiments of FIGS. 4A, 4B and 4C illustrates frame 74 as being oriented at an approximately 25-degree angle from the plane of the support structure 63, other suitable angular geometries can be employed, such as, e.g., 15-45 degrees. In particular, the angular configuration of body member 61 or frame 74 can be adjusted according to a desired illumination path from light source 62 to test strip 16. In other words, the total distance of the illumination path, which can range from approximately 10 to 30 mm in length in other embodiments, when projected on a two-dimensional plane, can be increased or decreased relative to the angular configuration of body member 61 or frame 74. The illumination path of light source 62 can be further defined based on the placement and/or arrangement of reflective surfaces 68. For example, in the embodiments of FIGS. 4A, 4B, and 4C, reflective surfaces 68 are equidistantly and angularly displaced from one another, thereby creating a generally triangular illumination path, while in other embodiments this particular configuration may vary.

In addition, the type of geometry described above which features, in particular, reflective surfaces 68 at an angle relative to the directed light by light sources 62 and light sensor 66 allows the use of high luminosity and efficient through-hole light source components, such as through-hole LEDs. These types of LEDs allow for light of a high luminosity to be directed in a precise manner at the test strip 16 being analyzed, while being more efficient in their battery use, causing less heat dissipation and being more cost effective than comparable board-mounted components. This also allows for a more compact design of the device. Moreover, the geometrical arrangement of reflective surfaces 68 allows for the use of multiple light sources 62 of different central wavelengths and luminosities. This can be particularly advantageous in that each light path of light sources 62 can have identical geometries from the light source 62 to the test strip 16 and in return to the light sensor 66, which facilitates the design of the device and the analysis algorithms in the application software of mobile device 15.

The exemplary embodiments of FIGS. 4A, 4B, and 4C are for illustration purposes only and the arrangement and/or configuration of optical sub-system 60 can vary in other embodiments specific to application and/or system requirements. For example, as depicted in FIG. 4C, the arrangement of reflective surfaces 68 allows for more illuminating light sources 62 of different wavelengths to be present.

Figure 5A:
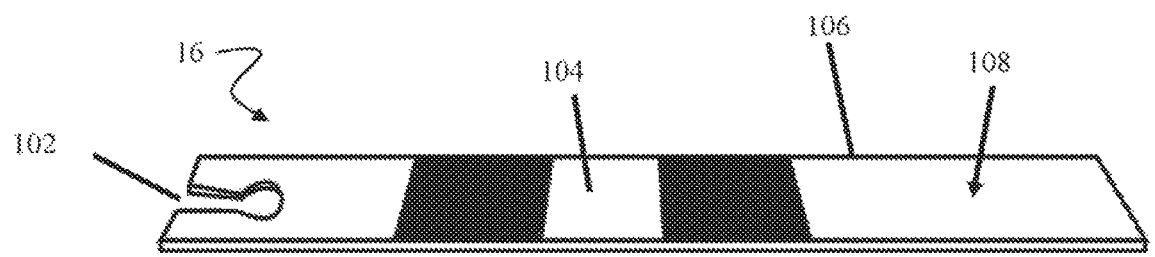
FIGS. 5A-5B depict an example of a colorimetric test strip used to measure an analyte concentration by causing a color reaction that is measured by the test strip reader.
Figure 5B:
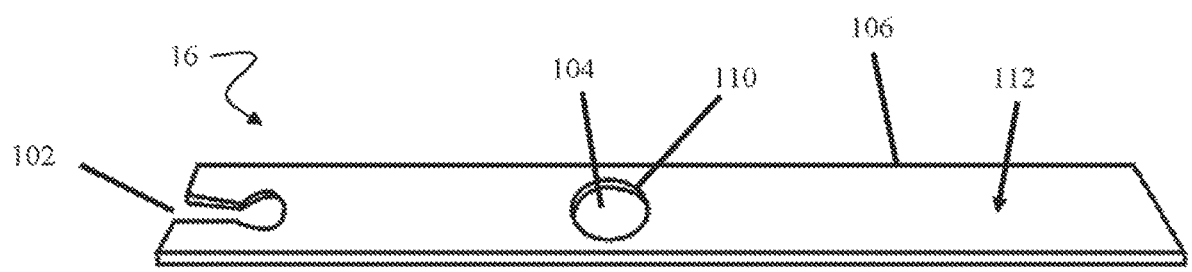

Referring to FIGS. 5A and 5B, a colorimetric test strip 16 is depicted for use with the test strip adapter 14 in an embodiment of the invention. One example of such a test strip 16 is the BETACHEK G5 test strip. In embodiments, test strip 16 includes a substrate 106 having a through hole 110 that is located substantially in the same location relative to an insertion end 102 as the reactive zone 104. Materials for a reactive zone 104 are disposed on a proximal face 108 of the colorimetric test strip 16 over the through hole 110, and are accessible from a distal face 112 of the colorimetric test strip 16 through the through hole 110. When the colorimetric test strip 16 is fully inserted in the test strip adapter 14, the through hole 110 is in alignment with the optical aperture 26 on the test strip adapter 14 and is accessible from the distal face 112. The alignment between the optical aperture 26 and the through hole 110 allows for the bodily fluid sample under test to be deposited onto the reactive area 104 of the proximal face 108 of the colorimetric test strip 16 after insertion into the test strip reader 10.

The colorimetric strips of FIGS. 5A and 5B are representative of a two-sided strip wherein the bodily fluid (e.g., a blood droplet) is applied to one side and the reactive change is observed on the other. When two-sided strips are utilized, the firmware controlling test strip reader 10 can be programmed by the software application controlling the mobile device 15 to observe the onset of the color change in a time-lapsed fashion and to acquire the reflected color signal of the reactive segment of the two-sided strip at a predetermined time interval after the onset. The digital signal acquired at the predetermined time interval can then be analyzed to provide the test results. The predetermined time can be established at a time period known to provide repeatable results, thereby enhancing the accuracy and reliability of the measurement.

In other embodiments, a single sided test strip 16 can be used that allows for the bodily fluid under test, which in some cases can comprise a bodily fluid sample pre-mixed with a reagent, to be applied directly to the reactive zone 104. Once the fluid sample is applied, the reactive zone 104 develops a color, which can then be detected after test strip 16 is inserted into the test strip reader 10. In this embodiment, test strip 16 is designed such that test strip 16 is inserted into test strip reader 10 only after the fluid sample is applied to the test strip. Similar colorimetric test strips are described in U.S. Patent Application Publication No. 2014/0072189, disclosures of which are incorporated by reference herein.

Figure 6A:
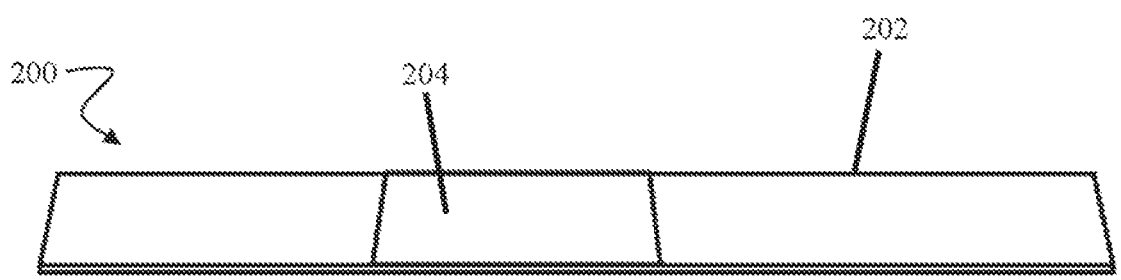
FIGS. 6A-6B depict an example of a mock test strip for use in device-to-device compensation according to embodiments.
Figure 6B:
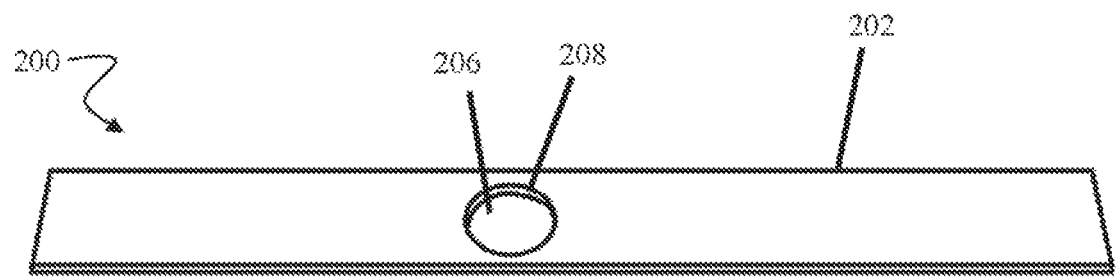

Referring to FIGS. 6A and 6B, a mock test strip 200 is depicted for use in the device-to-device compensation procedure of test strip reader 10, which is discussed with reference to FIG. 12. Each unit of test strip reader 10 has small variations in the performance of its individual components, such as the light sources 62, light sensor 66, reflective surfaces 68, as well as small manufacturing variations in the geometry of its housing 12, test strip adapter 14, and body member 61. These variations cause a change in the signal observed by light sensor 66 across different manufactured units, which can be compensated by one or several mock test strips 200. In embodiments, a mock test strip 200 can comprise a substrate 202, a reference material 204 with one side with a color area 206 printed with a known color that is visible through an aperture 208 formed in substrate 202. In another embodiment, mock test strip 200 can comprise substrate 202 solely, which is of a known color. In that case, no reference material 204 or aperture 208 is necessary, as the substrate itself is used as the material of known color.

Figure 7A:
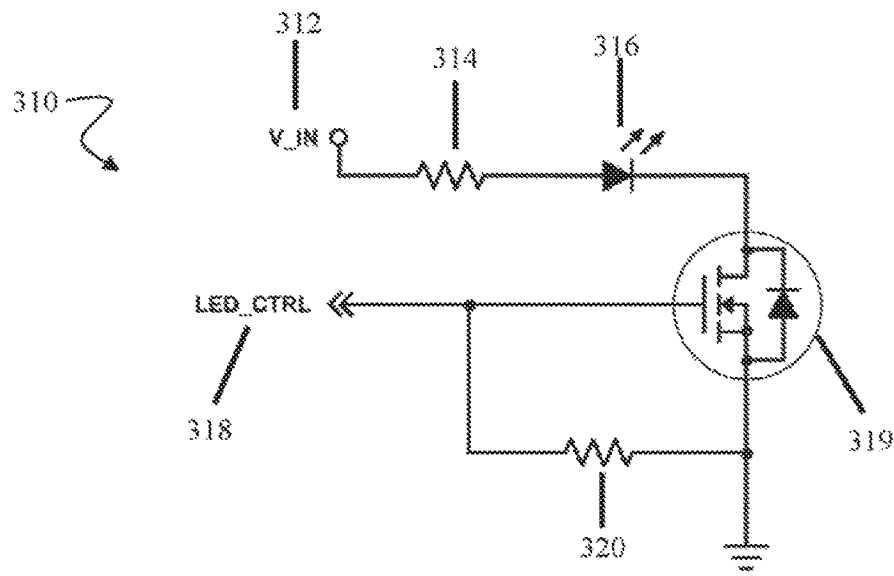
FIGS. 7A-7B depict schematic views of LED circuits according to two embodiments.
Figure 7B:
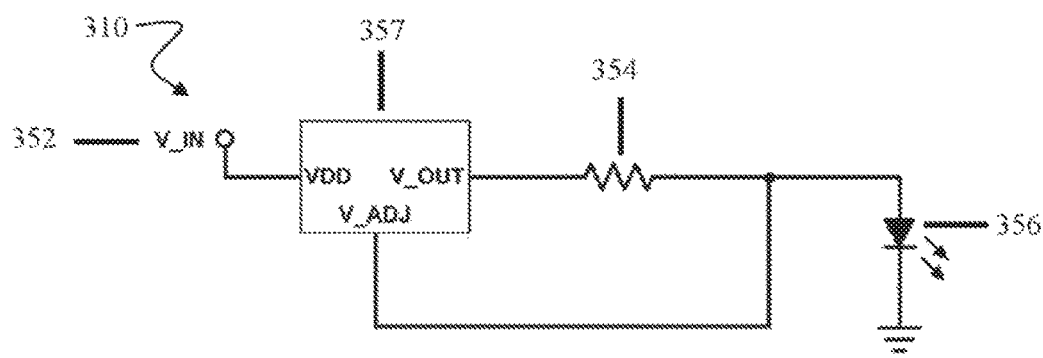

Referring to FIGS. 7A and 7B, a schematic view of a LED circuit 310 is depicted according to two embodiments. In one embodiment, LED circuit 310 can comprise a supply voltage 312, a current setting resistor 314, which together power a LED 316. LED 316 is toggled between an off and on states using a modulating signal 318, which is connected to a ground potential through a resistor 320, and that is applied to a gate terminal of a FET transistor 319 to control the FET transistor 319. This allows the effective brightness of LED 316 to be adjusted through pulse-width modulation (PWM) by rapidly switching LED 316 on and off at different rates. In other embodiments, referring now to FIG. 7B, LED circuit 310 can comprise a supply voltage 352, a constant voltage source 357, a current setting resistor 354, which together power a LED 356. Although not depicted in FIGS. 7A and 7B, in still other embodiments, the LED circuit 310 can be activated by strip switch 32 as previously discussed, which detects the presence of test strip 16. Such an arrangement is advantageous in that it assures test strip 16 is properly secured in test strip receiving channel 25 before an analysis is performed. The arrangement can also prevent inadvertent activation of light sources 62, which in turn helps to minimize the amount of power consumed by test strip reader 10.

Figure 8:
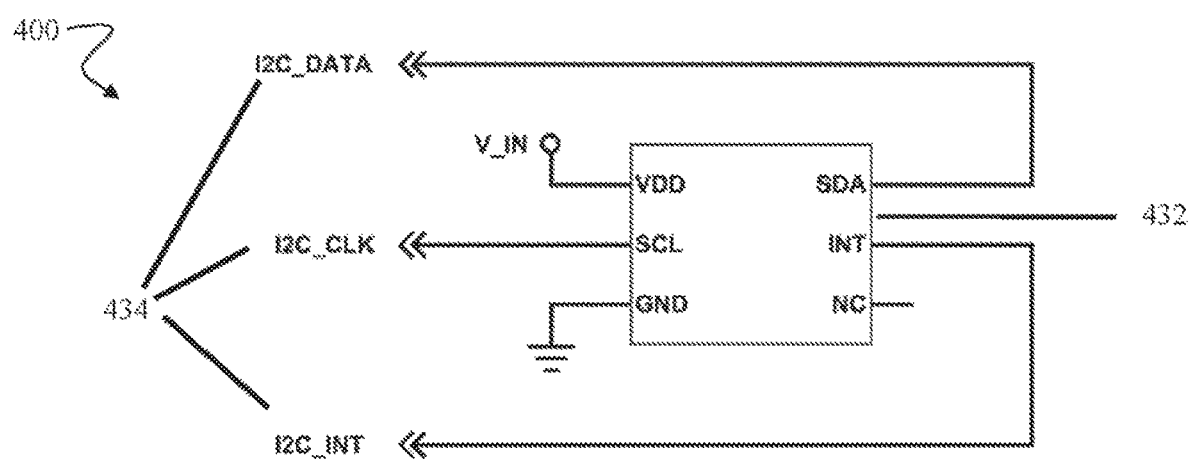
FIG. 8 depicts a schematic view of a sensor circuit according to an embodiment.

Referring to FIG. 8, a schematic view of a light sensor circuit 400 is shown according to an embodiment. In this embodiment, light sensor circuit 400 can comprise a digital light sensor integrated chip 432, which uses built-in analog photodiode circuits and color filters to detect the level of incoming light at different wavelengths. In this embodiment, digital light sensor integrated chip 432 communicates to the rest of the test strip reader 10 digital values that are proportional to the amount of light that hits its sensors in wavelength ranges defined by each of its channels' response spectra, over a certain time duration that is called the integration time. This communication can be accomplished using the I2C communication protocol using I2C pins 434. One example of such a digital light sensor integrated chip 432 is the AMS-TAOS TCS3472. In other embodiments, light sensor circuit 400 can be built directly from analog photodiodes, but using a digital integrated chip 432 offers a simpler design that while still includes analog photodiodes and color filters, is optimized, and standardized by the manufacturer of the integrated chip.

Figure 9:
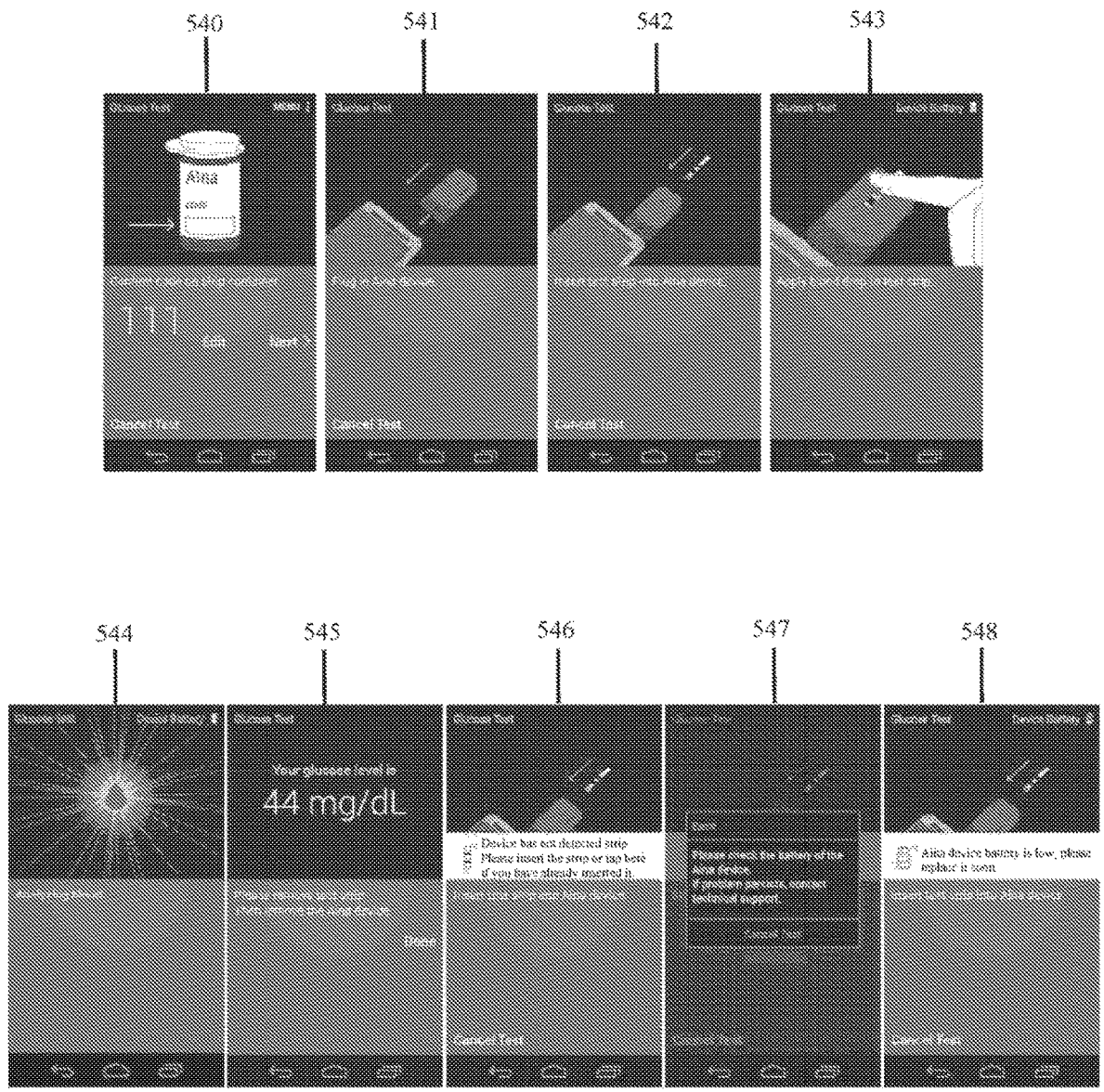
FIG. 9 depicts examples of graphical user interfaces according to an embodiment.

Referring to FIG. 9, a set of example user interfaces 540-548 displayed by the mobile device 15 to a user during the analyte testing process is shown. In one embodiment, at the start of an analyte test sequence, the user is shown a test strip calibration code selection screen 540. After confirming this code, the user is requested to connect test strip reader 10 to mobile device 15 with screen 541. Following this, the user is requested to insert test strip 16 in screen 542. Next at screen 543, the user is requested to apply a bodily fluid sample to test strip 16. Once a bodily fluid sample is received, the mobile device 15 interface notifies the user that the analysis is in progress with screen 544, and upon completion of the test, the user is presented with an analyte concentration reading in screen 545.

In addition, a user interface can comprise a plurality of error screens, such as error screens 546-548 to provide warning and error messages to a user utilizing mobile device 15. In particular, during use, an error message may occur that will cause either the analyte test sequence to stop running or warn a user that an error has occurred. For example, error screens 546 and 548 provide warning messages to a user, but do not prevent the analyte test sequence from being completed. In contrast, an error message received on screen 547 will cause the application on mobile device 15 to quit, thereby preventing a user from completing the analyte test sequence until the problem causing the error is rectified.

Figure 10:
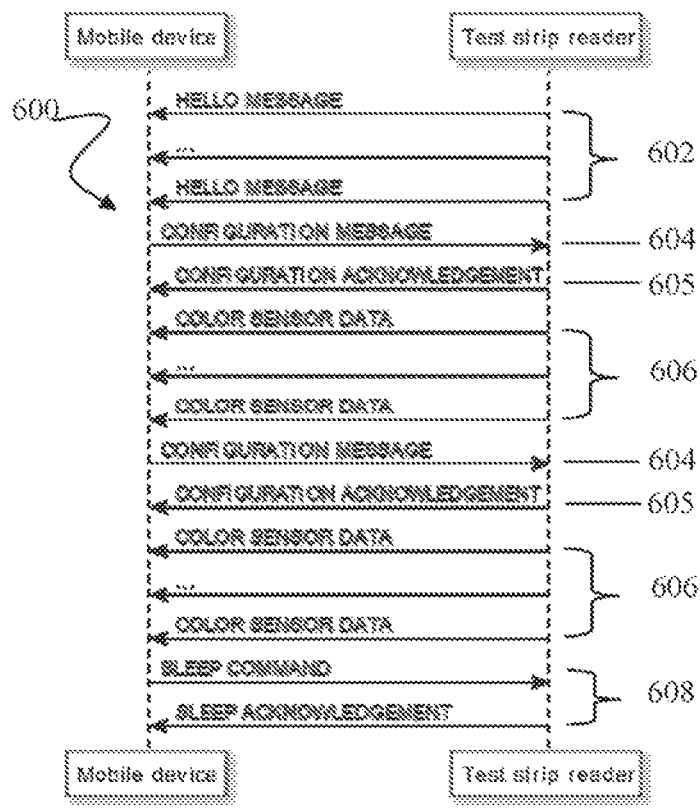
FIG. 10 depicts a flow diagram of a communication sequence between the test strip reader and a mobile device for use in an embodiment.

In operation and referring now to FIG. 10, a flow diagram of a typical communication sequence 600 between mobile device 15 and test strip reader 10 when performing an analyte test sequence is illustrated. When test strip reader 10 is powered on at 602, it can continuously send a "HELLO MESSAGE" to mobile device 15 via a communication port such as, e.g., the audio jack port of mobile device 15 as illustrated in embodiments herein. This "HELLO MESSAGE" can contain a device serial number, device diagnostic information, the device software version number and device specific compensation data that has been previously stored in the device's non-volatile memory. This compensation data is described in further detail below. After mobile device 15 receives this "HELLO MESSAGE", at 604, it can send a "CONFIGURATION MESSAGE" that contains a blinking sequence that test strip reader 10 can use to analyze colorimetric test strip 16 (refer, e.g., to FIG. 1) that is inserted into test strip reader 10.

In one embodiment, this blinking sequence can either use a single light source 62, in which case it can specify the luminosity of the light source when turned on (for instance via a pulse-width modulation duty cycle parameter), the period of time elapsed between successive light sources blinks, the duration that the light source stays on during a blink and light sensor 66 parameters such as its electronic gain and integration time. In another embodiment, this blinking sequence can use a plurality of light sources 62, in which case it can specify the parameters as listed above, but for each of the light sources 62, in addition to the order in which light sources 62 should blink. As an alternative to continuously powering on light sources 62, the blinking sequence as described above can be used as a power consumption reduction technique to minimize the battery use of test strip reader 10, while still sampling in time the color of the reaction area of test strip 16 inserted into test strip reader 10.

Different blinking sequences can be configured for different stages of the analyte test sequence, different test strip manufacturing lots and different test strip types (for different analytes) using a test strip code number. In one embodiment, the blinking sequences can correspond to a test strip code number and can be permanently stored in the application software or as a file on mobile device 15. In another embodiment, files with the blinking sequences can be stored on test strip reader 10 and transferred to mobile device 15 as needed. In yet another embodiment, a file containing the blinking sequences can be downloaded from a server via the internet by mobile device 15 when needed based on the test strip type and a test strip code number using for instance Wi-Fi or cellular internet networks. This embodiment offers the advantage of allowing the manufacturer to update the blinking sequences as needed remotely, namely, light sensor 66 parameters such as electronic gain and integration, as well as the effective brightness of light sources 62, which offers more stability with respect to the characteristics of light sensor 66, light source 62 components and test strips 16 that can vary between different manufacturing lots. Moreover, the blinking sequence downloading feature allows new manufacturing lots of test strips 16 to be supported after test strip reader 10 is dispatched to the user because it only requires that a file containing the new blinking sequences be downloaded by mobile device 15. Other parameters such as the allowed ambient temperature range and permitted battery voltage values can also be updated remotely in this manner.

In addition, the modularity of the definitions of the blinking sequences allows the possibility of adding support for testing of new analytes with an over-the-air or physical software update to mobile device 15 software without having to change the software on test strip reader 10, which is usually a complex task for users to perform for such embedded devices. These over-the-air software updates can also include completely new algorithms that would be needed to analyze the kinetic or end-point reactions of test strips 16 for the new analytes. Since test strip reader 10 can contain a plurality of light sources 62 that can have different central wavelengths, it is particularly suitable for the analysis of multiple types of analytes, including new ones that are conceived after test strip reader 10 is delivered to the user.

Next in communication sequence 600, at 605, once test strip reader 10 receives the "CONFIGURATION MESSAGE", it can then configure itself with the specified blinking sequence, replying with a "CONFIGURATION ACKNOWLEDGEMENT" to mobile device 15 when this process is done. Test strip reader 10 can then go through the blinking sequence as specified. Following each blink in the blinking sequence, at 606, test strip reader 10 can send "COLOR SENSOR DATA" which it measured during that blink. This "COLOR SENSOR DATA" can contain the sensor data values $\{I_c\}$ from one or several color channels c of light sensor 66 of test strip reader 10, device diagnostic information such as the ambient temperature and battery level, an identification of the light source used in this particular blink and a sequence number that grows sequentially with each successive "COLOR SENSOR DATA" to allow detection any potential loss of data by the mobile device's application software.

Mobile device 15 receives this "COLOR SENSOR DATA" and can process it according to algorithms defined in its corresponding software to analyze the color reaction of test strip 16 inserted into test strip adapter 14 of test strip reader 10. This can include giving the user feedback through the screen, audio output or vibration motor of mobile device 15 about the progress of the analysis, or any errors such as for example an ambient temperature out of range or low battery.

At any point during the analysis, illustrated at 604 in FIG. 10, mobile device 15 can send a new "CONFIGURATION MESSAGE" to test strip reader 10 with a new blinking sequence that test strip reader 10 should use. This feature can be used to allow to optimize the battery use of test strip reader 10 by using a faster blinking sequence, meaning with a lower period of time between successive blinks, only at specific points in the color reaction of the test strip when it is necessary to measure the color reaction with more time granularity.

Once mobile device 15 has received enough "COLOR SENSOR DATA" from test strip reader 10 that fully defines the kinetic or end-point color reaction of the test strip 16 that it is analyzing, the application on mobile device 15 can compute and show the analyte concentration reading to the user on mobile device 15 screen. In another embodiment, mobile device 15 can send this reading to another software application on mobile device 15, or send it through the internet to a server that can store this data.

At 608, mobile device 15 can then send a "SLEEP COMMAND" that test strip reader 10 answers with a "SLEEP ACKNOWLEDGEMENT" before going to a deep sleep mode in order to save battery power. In an embodiment, at any point in this sequence the test strip reader 10 can be powered off by toggling strip switch 32 utilizing the same methods as discussed with reference to FIG. 2B.

Figure 11:
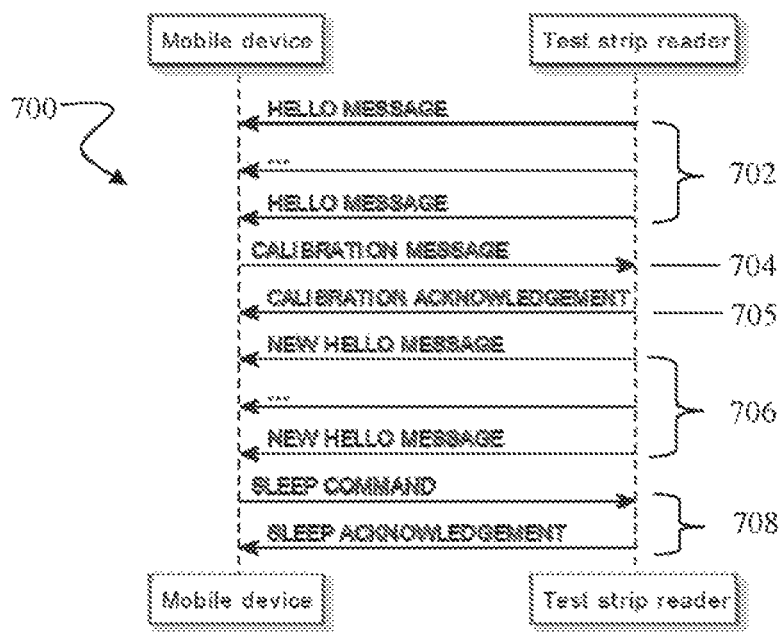
FIG. 11 depicts a flow diagram of a communication sequence between the test strip reader and a mobile device for use in an embodiment for storing device specific compensation data.

Referring to FIG. 11, a method 700 for storing device specific compensation data for the test strip reader 10 utilizing mobile device 15 is depicted. Storing of this device specific compensation data of test strip reader 10 can occur during the manufacturing process or can be performed by an end user.

At 702, after test strip reader 10 is powered on, it can continuously send a "HELLO MESSAGE" to mobile device 15 via a communication port of mobile device 15. After mobile device 15 receives the "HELLO MESSAGE", then at 704 it can send test strip reader 10 a "CALIBRATION MESSAGE" that contains new device specific compensation data that test strip reader 10 should store in its non-volatile memory. At 705, test strip reader 10 receives this "CALIBRATION MESSAGE" and answers with a "CALIBRATION ACKNOWLEDGEMENT" once it has stored this device specific compensation data in its non-volatile memory. Test strip reader 10 at 706 then goes back to continuously sending a "NEW HELLO MESSAGE" that contains the new device specific compensation data that it stored in its non-volatile memory. Next at 708, mobile device 15 can then send a "SLEEP COMMAND" that test strip reader 10 answers with a "SLEEP ACKNOWLEDGEMENT" before going to a deep sleep mode in order to save battery power. In an embodiment, at any point in this sequence test strip reader 10 can be powered off by toggling its strip switch 32. As discussed with reference to FIG. 2B, in one embodiment, strip switch 32 is toggled by the removal of a test strip 16 from test strip adapter 14.

Figure 12:
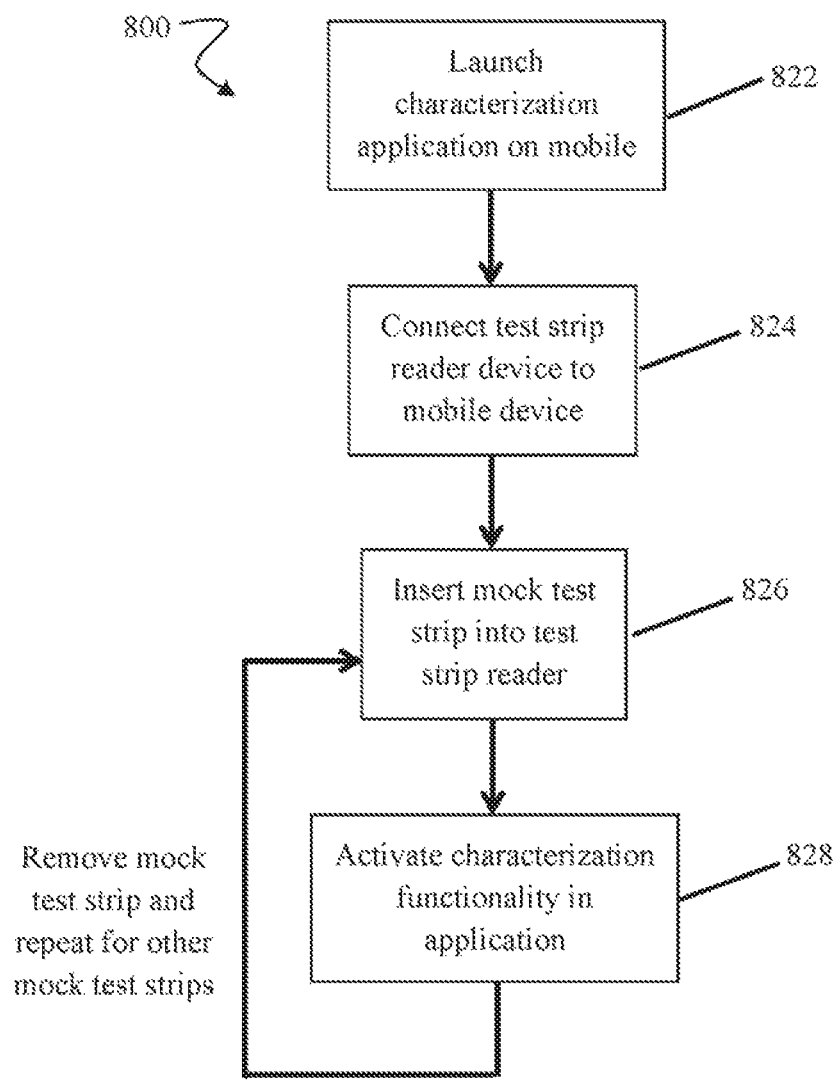
FIG. 12 depicts a flow diagram of a process for device-to-device compensation according to an embodiment.

Referring to FIG. 12, a method 800 for characterizing the optical characteristics of a given device by generating and storing device-to-device compensation data in the device's non-volatile memory is depicted for use in an embodiment. The characterization method 800 can be used to compensate for small variations in the performance of individual components of test strip reader 10, such as the light sources 62, light sensor 66, reflective surfaces 68, as well as small manufacturing variations in the geometry of the plastics of test strip reader 10.

At the first step 822, the characterization application can be launched on mobile device 15. Next at step 824, test strip reader 10 can be connected to mobile device 15. Once an acknowledgement is received in the user interface of mobile device 15, then at 826, a mock test strip 200 with a color area 206 of known constant color can be inserted into test strip reader 10. In an embodiment, this insertion toggles strip switch 32 and powers on test strip reader 10, which causes it to enter step 702 as discussed with reference to FIG. 11, and to continuously send a "HELLO MESSAGE" to mobile device 15.

At step 828, utilizing the user interface of the characterization application running on mobile device 15, an algorithm, which utilizes a function to determine device specific compensation data, is initiated. This in turn causes the software on mobile device 15 to configure test strip reader 10 with a "CONFIGURATION MESSAGE" that contains a blinking sequence as described above with reference to FIG. 10. Upon receipt of the "CONFIGURATION MESSAGE," test strip reader 10 will then begin sending "COLOR SENSOR DATA" according to the blinking sequence it has been configured to use. As previously discussed, "COLOR SENSOR DATA" can include sensor data values $\{I_c\}$, device diagnostic information, light source identification information, as well as other relevant device status data. After the software on mobile device 15 receives one or several such "COLOR SENSOR DATA", mobile device 15 will compute the device specific compensation data for the mock test strip that was used. This process can be repeated with several different mock strips if required to compute the full compensation data across different mock test strip colors. This set of different mock test strips can be designed to span the reflected colors that the test strip reader will see during various analyte testing.

During device characterization, test strip reader 10 can be configured as either a reference "master" unit or a regular "production" unit. For example, if test strip reader 10 used in the device characterization method 800 is a reference "master" unit, the resulting compensation data is referred to as the reference compensation data $\{M_{s,p}\}$. This reference compensation data $\{M_{s,p}\}$ for each mock test strip s and for each set of imaging parameters p can be stored for later use by mobile devices 15 when performing analyte test sequences. In one embodiment, this reference compensation can be included in the application software distributed on mobile device 15 used during future analyte test sequences. In another embodiment, this reference compensation data can be stored in a file on a server that can be accessed by mobile device 15 during an analyte test sequence via the internet using Wi-Fi or mobile cellular networks. Allowing mobile device 15 to retrieve this reference compensation data remotely allows the reference "master" unit used by the manufacturer to collect master compensation data to be changed whenever needed, which reduces the dependency on a single "master" unit that needs to be safeguarded over the lifetime of the product.

The imaging parameters p can include the light source 62 to be used, the effective brightness of the light source 62 when turned on, the duration that the light source 62 stays on during a blink, and light sensor 66 parameters such as its electronic gain and integration time. In one embodiment, the reference compensation data $\{M_{s,p}\}$ can consist simply of light sensor values recorded by light sensor 66 for each mock test strip s and for each set of imaging parameters p when measuring the color area 206 of known constant color of mock test strip 200.

Contrarily, if test strip reader 10 used in the device characterization method 800 is a regular "production" unit, the resulting compensation data is referred to as the device specific compensation data $\{D_{s,p}\}$. This device specific compensation data $\{D_{s,p}\}$ for each mock test strip s and for each set of imaging parameters p can be sent to test strip reader 10 by mobile device 15 via a "CALIBRATION MESSAGE" as described in step 704 of method 700 for storing device specific compensation data, which can cause test strip reader 10 to store the device specific compensation data in its non-volatile memory. After this step, the particular reader is considered calibrated and can be used for analyte testing. In one embodiment, the device specific compensation data $\{D_{s,p}\}$ can consist simply of light sensor values recorded by light sensor 66 for each mock test strip s and for each set of imaging parameters p when measuring the color area 206 of known constant color of mock test strip 200. Since the only required material for performing the device-to-device characterization method 800 on a regular "production" test strip reader 10 unit is the characterization application software to run on the mobile device 15 and one or several mock test strips 200, this method can be performed both during the manufacturing process and also by an end user if needed.

During a regular analyte test sequence that follows the sequence described in FIG. 10, mobile device 15 software receives a "HELLO MESSAGE" that contains device specific compensation data $\{D_{s,p}\}$ stored in test strip reader 10's non-volatile memory. For a specific set of imaging parameters p that can be requested by mobile device 15 through its "CONFIGURATION MESSAGE", mobile device 15 software computes a compensation function based on reference compensation data $\{M_{s,p}\}$ stored in the mobile software or obtained from a remote server as previously described, and device specific compensation data $\{D_{s,p}\}$ received from test strip reader 10 in its "HELLO MESSAGE". Each subsequent light sensor value $I_{c,p}$ for a specific color channel c and set of imaging parameters p received by mobile device 15 from test strip reader 10 in "COLOR SENSOR DATA" can be compensated before use in analysis algorithms using an equation of the following form to map it to the equivalent value on the reference "master" unit:

$$I_{c,p}^* = f(\{M_{s,p}\}, \{D_{s,p}\}, I_{c,p})$$

where the compensation function $f(.)$ can be a mathematical function such as a polynomial, or a look-up table. This equation yields the compensated light sensor value $I^*_{c,p}$, which can then be used in subsequent analysis algorithms as if it was measured using the reference "master" unit. In one embodiment, the compensation function $f(.)$ can have the simple form:

$$f(\{M_{s,p}\}, \{D_{s,p}\}, I_{c,p}) = \frac{M_{s,p}}{D_{s,p}} I_{c,p}$$

where compensation data for a specific mock test strip s is used depending on which analyte is being tested, and which part of the test strip color reaction is being analyzed, for a certain set of imaging parameters p.

Use of this simple form is possible because of key elements in the design of the test strip reader 10, such as the optical geometry, which allows the use of high luminosity light sources 62 and directly guide a large portion of the light from the light sources 62 to the test strip 16 being analyzed. Another aspect that contributes to this is the small form factor of the device that, combined with the optical geometry, minimizes the total projected distance of the light path from the light sources 62 to the light sensor 66. This design allows for a predictable linear response of the optical system when imaging test strip reaction colors close to the known colors the mock test strips used in the device-to-device compensation described above, because of an optimal rejection of ambient light and the isolation of other variables such as spread of the light beam with distance, which in turn allows for the use of the simple compensation function listed above and a small number of mock test strips 200. Using the simplest possible compensation function is desirable because it will produce the most consistent and reproducible results.

In one embodiment, a test strip reader can be provided to a user in the form of a kit which includes a test strip reader according to any of the embodiments described herein, and a set of instructions for using the test strip reader as described herein. The kit may comprise one or more hermetically sealed packages that can include test strips 16 for one or more analytes, the mock test strips 200, lancets, etc. that are needed for operating and maintaining the test strip reader 10, and performing analyte testing. The instructions may be provided as part of the kit, or indications may be provided linking a user to electronically accessible instructions. The instructions can be any of a variety of tangible or intangible media including, but not limited to a written manual, a separate screen inside of the application software running on the mobile device 15 for analyte testing, a CD or CD-ROM, DVD, BluRay, digitally downloadable or viewable on onto a personal device, such as a computer, tablet, smart device, and/or via verbal instruction by a provider of the kit. In another embodiment, the instructions are provided, for example, by a manufacturer or supplier of the assemblies, separately from providing the assemblies, such as by way of information that is accessible using the Internet or by way of seminars, lectures, training sessions or the like. The kit and/or the separate components of the kit may be provided by causing the kit and/or components to be manufactured and made available to a user.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the scope of the invention, as defined by the claims. Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

Any incorporation by reference of documents above is limited such that no subject matter is incorporated that is contrary to the explicit disclosure herein. Any incorporation by reference of documents above is further limited such that no claims that are included in the documents are incorporated by reference into the claims of the present Application. The claims of any of the documents are, however, incorporated as part of the disclosure herein, unless specifically excluded. Any incorporation by reference of documents above is yet further limited such that any definitions provided in the documents are not incorporated by reference herein unless expressly included herein.

For purposes of interpreting the claims for the present invention, it is expressly intended that the provisions of Section 112(f) of 35 U.S.C. are not to be invoked unless the specific terms "means for" or "step for" are recited in a claim.

The invention claimed is:

1. A multi-analyte testing analyzer for use with a mobile device comprising:
   a test strip reader configured to removably receive a test strip having a bodily fluid sample, the test strip reader including:
      a housing including structure defining a test strip receiving channel;
      a light source within the housing, the light source including at least two light emitting diodes each positioned proximate a corresponding angled reflective surface to direct light from the reflective surface toward the test strip receiving channel, wherein the corresponding angled reflective surfaces are each inclined at a common angle of between 15-45 degrees relative to a direction defined by a beam of light emitting from said corresponding light emitting diode to direct light from said reflective surface toward said test strip receiving channel along a light path from the light emitting diode to the corresponding angled reflective surface to the test strip and back to the light sensor that is between 10-30 mm in length;
      a light sensor within said housing to sense light reflected from the test strip when positioned in the test strip receiving channel; and
      control circuitry configured to:
         receive a control sequence from the mobile device,
         control the light source in response to the control sequence,
         generate a set of data values corresponding to a measured light intensity from the light sensor during the control sequence, and
         transmit the set of data values to the mobile device; and
      a battery positioned within the housing and operably connected to the light source, the light sensor and the control circuitry; and
   a software application configured to execute on the mobile device to:
      analyze the set of data values from the test strip reader to determine an analyte concentration in the bodily fluid sample; and
      display the analyte concentration on a graphical user interface of the mobile device.

2. The multi-analyte testing analyzer of claim 1, wherein the software application is configured to analyze the set of data values from the test strip reader to optically assess a change in color profile based on the measured light intensity reflected from the test strip and determine the analyte concentration in the bodily fluid sample based on the change in color profile.

3. The multi-analyte testing analyzer of claim 1, wherein the bodily fluid sample comprises a sample selected from the group consisting of blood, urine, and saliva.

4. The multi-analyte testing analyzer of claim 1, wherein the control sequence includes a blinking sequence that instructs the control circuitry to vary at least one of a blink, a duration, an order, or a luminosity of the at least two light emitting diodes.

5. The multi-analyte testing analyzer of claim 4, wherein the control sequence is downloaded to the mobile device over the Internet.

6. The multi-analyte testing analyzer of claim 4, wherein the mobile device is provided with a plurality of control sequences, each control sequence associated with a different analyte to be analyzed.

7. The multi-analyte testing analyzer of claim 6, wherein the different analyte to be analyzed is determined based on a code on the test strip that is used to determine which of the plurality of control sequences the mobile device sends to the test strip reader.

8. The multi-analyte testing analyzer of claim 4, wherein the light source and the light sensor includes a plurality of color channels, and the signal to the mobile device includes an identification of the color channel used in a corresponding blink of the light source.

9. The multi-analyte testing analyzer of claim 4, wherein the signal to the mobile device includes diagnostic information selected from one or more of an ambient temperature of the test strip reader, a level of the battery of the test strip reader, and a sequence number for each set of data values.

10. The multi-analyte testing analyzer of claim 1, wherein the software application is further configured to transmit a configuration profile to the test strip reader that causes the control circuitry of the test strip reader to execute a device characterization based on the configuration profile to generate compensation data that can be used to compensate for device variations of the test strip reader.

11. The multi-analyte testing analyzer of claim 1, wherein the software application is further configured to receive compensation data from the test strip reader that is used to analyze the set of data values to compensate for device variations of the test strip reader.

12. The multi-analyte testing analyzer of claim 1, wherein the light source of the test strip reader includes three light emitting diodes equidistantly angularly arranged relative to the other of the light emitting diodes.

13. The multi-analyte testing analyzer of claim 1, wherein the light source of the test strip reader includes three light emitting diodes each positioned at a right angle to at least one other of the light emitting diodes.

* * * * *